(12) United States Patent
Kay et al.

(10) Patent No.: US 7,811,608 B2
(45) Date of Patent: *Oct. 12, 2010

(54) TISSUE REPAIR COMPOSITIONS AND METHODS FOR THEIR MANUFACTURE AND USE

(75) Inventors: John F. Kay, Carlsbad, CA (US); Mark Borden, Lake Forest, CA (US); Richard Coulson, Vancouver (CA); Edward King, Inglewood, CA (US)

(73) Assignee: Isotis Orthobiologics, Inc., Irvine, CA (US)

( * ) Notice: Subject to any disclaimer, the term of this patent is extended or adjusted under 35 U.S.C. 154(b) by 783 days.

This patent is subject to a terminal disclaimer.

(21) Appl. No.: 11/459,972

(22) Filed: Jul. 26, 2006

(65) Prior Publication Data

US 2006/0251729 A1 Nov. 9, 2006

Related U.S. Application Data

(63) Continuation of application No. 10/195,671, filed on Jul. 15, 2002, now Pat. No. 7,132,110.

(60) Provisional application No. 60/316,005, filed on Aug. 30, 2001.

(51) Int. Cl.
*A61K 35/32* (2006.01)
*A61K 38/18* (2006.01)

(52) U.S. Cl. ......................................... 424/549; 514/12

(58) Field of Classification Search ....................... None
See application file for complete search history.

(56) References Cited

U.S. PATENT DOCUMENTS

| 4,394,370 | A | 7/1983 | Jefferies ..................... 424/15 |
|---|---|---|---|
| 4,440,750 | A | 4/1984 | Glowacki et al. ............ 424/572 |
| 4,563,350 | A | 1/1986 | Nathan et al. .................. 424/95 |
| 4,627,982 | A | 12/1986 | Seyedin et al. ................ 424/95 |
| 4,902,296 | A * | 2/1990 | Bolander et al. ......... 623/23.63 |
| 4,971,954 | A | 11/1990 | Brodsky et al. ............... 514/21 |
| 5,108,753 | A | 4/1992 | Kuberasampath et al. ... 424/422 |
| 5,236,456 | A | 8/1993 | O'Leary et al. ............... 623/16 |
| 5,244,577 | A | 9/1993 | Notoya et al. ............... 210/641 |
| 5,284,655 | A | 2/1994 | Bogdansky et al. ......... 424/422 |
| 5,290,558 | A | 3/1994 | O'Leary et al. ............. 424/422 |
| 5,371,191 | A | 12/1994 | Poser et al. ................. 530/350 |
| 5,405,390 | A | 4/1995 | O'Leary et al. ............. 424/422 |
| 5,516,532 | A | 5/1996 | Atala et al. .................. 424/548 |
| 5,531,791 | A | 7/1996 | Wolfinbarger, Jr. ............ 623/16 |
| 5,676,146 | A | 10/1997 | Scarborough ................ 128/654 |
| 5,707,962 | A | 1/1998 | Chen et al. .................... 514/12 |
| 5,877,287 | A | 3/1999 | Lilja et al. ................... 530/355 |
| 5,908,921 | A | 6/1999 | La Roche et al. ............ 530/354 |
| 5,968,556 | A | 10/1999 | Atala et al. .................. 424/548 |
| 6,030,635 | A | 2/2000 | Gertzman et al. ............ 424/423 |
| 6,080,843 | A | 6/2000 | Rainville et al. ............. 530/355 |
| 6,123,731 | A | 9/2000 | Boyce et al. .............. 623/23.63 |
| 6,180,605 | B1 | 1/2001 | Chen et al. ..................... 514/12 |
| 6,180,606 | B1 | 1/2001 | Chen et al. ..................... 514/12 |
| 6,189,537 | B1 | 2/2001 | Wolfinbarger, Jr. .......... 128/898 |
| 6,281,195 | B1 | 8/2001 | Rueger et al. .................. 514/21 |
| 6,305,379 | B1 | 10/2001 | Wolfinbarger, Jr. .......... 128/898 |
| 6,426,332 | B1 | 7/2002 | Rueger et al. .................. 514/21 |
| 6,437,018 | B1 | 8/2002 | Gertzman et al. ............ 523/116 |
| 6,458,375 | B1 | 10/2002 | Gertzman et al. ............ 424/423 |
| 6,599,520 | B2 * | 7/2003 | Scarborough et al. ....... 424/426 |
| 6,627,230 | B2 | 9/2003 | Benedict et al. ............. 424/549 |
| 7,132,110 | B2 * | 11/2006 | Kay et al. .................... 424/423 |
| 2002/0018796 | A1 | 2/2002 | Wironen ...................... 424/423 |
| 2002/0076429 | A1 | 6/2002 | Wironen et al. ............. 424/426 |
| 2002/0098222 | A1 | 7/2002 | Wironen et al. ............. 424/423 |
| 2002/0192263 | A1 | 12/2002 | Merboth et al. ............. 424/426 |
| 2002/0197241 | A1 | 12/2002 | Boss, Jr. et al. ............. 424/93.7 |

FOREIGN PATENT DOCUMENTS

WO  WO 98/35653  8/1998

OTHER PUBLICATIONS

Bätge et al., *Eur. J. Biochem.*, 192:153-159 (1990).
Beghe et al., *Int'l. J. Tiss. Reac.*, XIV (Suppl.) 11-19 (1992).
Gerstenfeld et al., "Selective Extractability of Noncollagenous Proteins from Chicken Bone," *Calcif. Tissue Int.*, 55:230-235 (1994).
Miller and Gay, "Collagen: An Overview," *Methods in Enzymology*, 82A:3-32 (1982).
Nagai and Suzuki, "Isolation of collagen from fish waste material—skin, bone and fins," *Food Chemistry*, 68:277-281 (2000).
Nagumo et al., *Kitasato Arch. Exp. Med.*, 48:189-191 (1975).
Wang and Glimcher, "Characterization of Matrix-Induced Osteogenesis in Rat Calvarial Bone Defects: II. Origins of Bone-Forming Cells," *Calcif. Tissue Int.*, 65:486-493 (1999).
*Webster's II New Riverside Dictionary*, Houghton-Mifflin, Boston, MA, pp. 362 and 645 (1994).
Sampath et al., "Homology of Bone Inductive Proteins . . . ," *P.N.A.S. USA*, 80(21):6591-6595 (1983).
Office Action relating to corresponding EP Application No. 03754679.3, Mar. 16, 2010, pp. 1-3.

* cited by examiner

*Primary Examiner*—Jon P Weber
*Assistant Examiner*—Laura Schuberg

(57) ABSTRACT

An osteogenic composition is prepared by a process including the steps of subjecting demineralized bone to an extraction medium to produce an insoluble extraction product and a soluble extraction product, separating the insoluble extraction product and the soluble extraction product, drying the soluble extraction product to remove all or substantially all of the moisture in the soluble extracting product, and combining the dried soluble extraction product with demineralized bone particles. Preferably, the process does not involve heating.

19 Claims, 4 Drawing Sheets

TISSUE REPAIR COMPOSITIONS AND METHODS FOR THEIR MANUFACTURE AND USE

RELATED APPLICATION(S)

This application is a continuation of U.S. patent application Ser. No. 10/195,671, filed Jul. 15, 2002, which claims priority to U.S. provisional application No. 60/316,005, filed Aug. 30, 2001, each of which is hereby incorporated herein by reference in its entirety.

BACKGROUND OF THE INVENTION

Various compositions have been used to repair damaged tissues. Compositions are available to provide a scaffold to support new bone growth and/or to provide factors that induce new bone growth. Demineralized bone particles (also referred to as demineralized bone matrix or DBM) and bone morphogenetic proteins (BMPs) are two materials that have been used to enhance bone growth. For example, Jefferies (U.S. Pat. No. 4,394,370) discloses tissue repair compositions containing DBM, BMPs, or both in a reconstituted collagen matrix. Glowacki et al. (U.S. Pat. No. 4,440,750) discloses aqueous compositions of DBM and reconstituted collagen fibers.

DBM is generally composed of particles of bone tissue that have been specially treated, generally by soaking in acid to remove their mineral content. The resulting DBM is composed mainly of highly cross-linked collagen. The remaining non-collagenous proteins include proteins such as TGF-β, PDGF, osteopontin, osteonectin, BMPs, and others BMPs are a group of proteins categorized in the transforming growth factor beta super-family of proteins. To date, several BMPs have been isolated and associated with the bone healing process. BMPs can be isolated from bone as a mixture of proteins or produced individually through recombinant gene technology.

DBM may be used directly in bone repair compositions. See, e.g., Jefferies, supra; Glowacki et al., supra. However, in such compositions, the tissue repair factors are trapped within the highly cross-linked collagen network of the DBM. It is believed that the BMPs and other embedded tissue repair factors are slowly released as the collagen component of DBM is degraded. Therefore, the potential effectiveness of the tissue repair factors within the DBM is hindered. An alternative to slow release is to isolate the tissue repair factors from the DBM. Isolated and purified connective tissue repair factors have been used in bone repair compositions, but extraction, purification, and mixture with a dispersion medium or incorporation into a delivery vehicle requires multiple steps.

There is a need in the art for additional tissue repair compositions that employ tissue repair factors that are substantially freed of the cross-linked DBM collagen network and that do not require complicated extraction and purification steps.

SUMMARY OF THE INVENTION

This invention relates to tissue repair compositions comprising soluble and/or insoluble products from the extraction of DBM, and methods for their manufacture and use. These DBM-derived products, also referred to herein as the "soluble extraction product" and the "insoluble extraction product" may contain tissue repair factors and can be processed to produce a variety of formulations and consistencies.

The compositions according to the invention use the soluble and/or insoluble products from the extraction of DBM. The DBM extraction is generally conducted at room temperature in a suitable extraction medium. Following extraction, the soluble and insoluble extraction products are separated. These products may be further processed, for example, by centrifuging, decanting, filtering, titration, precipitation, dialyzing, fully or partially drying, rehydrating and sterilizing. In a preferred embodiment, these steps are performed without heating. These products may be used in a variety of connective tissue repair compositions, alone or in combination with other active or inactive ingredients.

In a preferred embodiment, the inventive compositions contain a rehydrated form of the dried soluble extraction product. The rehydrated soluble extraction product can be used alone or in a mixture with one or more active or nonactive ingredients. For example, the rehydrated soluble extraction product can be combined with one or more biologically active materials and a thickening agent. The physical properties of the resulting mixture(s), including viscosity, can be varied by modifying the relative concentrations of the soluble extraction product, the size of the pieces of dried soluble extraction product, the amount of water used for rehydration, the extent of any subsequent drying, and other soluble or insoluble ingredients. For example, the final composition may have the consistency of a gel, paste, putty or sponge.

The compositions according to the invention can be prepared for injection or insertion at, into, onto, or near bone defect sites, cartilage repair sites, or other musculoskeletal sites. The inventive compositions can also be used as a coating on surgical implants to be inserted at, into, onto, or near bone defect sites, cartilage repair sites, or other musculoskeletal sites. Accordingly, the invention is directed to an osteogenic surgical implant comprising surgical implant coated with the inventive osteogenic compositions and a method of treating a bone defect comprising providing a surgical implant, coating the surgical implant with the inventive osteogenic composition, and implanting the surgical implant at a bone defect site.

DESCRIPTION OF ILLUSTRATIVE EMBODIMENTS

Figure 1A:
FIG. 1A is a photograph of the composition from Example 1 plus residual putty implanted for 28 days in an athymic mouse. The photograph shows a bone ossicle (arrow) surrounding fatty bone marrow (BM). Residual material (R) is still present in this explant. Haematoxylin and eosin stain; original magnification ×200.

An osteogenic composition is prepared by a process including the steps of subjecting demineralized bone (DBM) to an extraction medium to produce an insoluble extraction product and a soluble extraction product, separating the insoluble extraction product and the soluble extraction product, drying the soluble extraction product to remove all or substantially all of the moisture in the soluble extraction product, and combining the dried soluble extraction product of step c) with demineralized bone particles. Preferably, the process does not involve heating.

The DBM used in the extraction process according to the invention can be prepared according to a variety of different methods. Conventional methods, such as those identified in Jefferies, supra, and Glowacki et al., supra are preferred. Such conventional methods for preparing DBM include a defatting step and a demineralization step. Different methods of defatting, e.g., hot water, or chloroform/methanol washes, can be used. Demineralization can be performed according to a variety of different methods, generally using different types of acid solutions for varying times and at variable temperatures, to remove all or substantially all of the mineral content from the bone.

For purposes of this invention, any shape and particle size of DBM may be used. This includes DBM in the form of fragments, slices, pellets, shavings, strips, granules, or powder as well as demineralized whole bones. Preferably, the demineralized bone is of small particle size, and most preferably in the form of granules or powder. Most preferably, the demineralized bone is in the form of particles having an average particle size of from about 100 to about 1000 microns, further preferable from about 125 to about 850 microns.

In the method for manufacturing the compositions according to the invention, DBM is placed in an aqueous-based medium capable of extracting collagen, gelatin, and/or connective tissue factors. This step is performed by a method that is different than conventional methods used to extract gelatin (LaRoche, et al. (U.S. Pat. No. 5,908,921), Lilja, et al. (U.S. Pat. No. 5,877,287), and Rainville, et al. (U.S. Pat. No. 6,080,843)), because it is performed at room temperatures and uses agitation unlike other described methods (e.g., as described in O'Leary, et al. (U.S. Pat. No. 5,236,456)). The extraction causes limited hydrolysis of chemical bonds within the collagen (Miller E. J. & Gay S., *Collagen: An Overview, In: Methods in Enzymology*, vol. 82 (A), pp. 3-32, 1982). This results in the production of a DBM-derived protein mixture previously characterized as water-soluble collagen and its lower molecular weight cleavage products, collectively referred to as "gelatin". (Rainville et al. supra; Nagumo et al. *Kitasato Arch. Exp. Med.* 48: 189-191, 1975; Batge et al., *Eur. J. Biochem.* 192: 153-159, 1990). Due to the hydrolytic cleavage of collagen's intra- and intermolecular bonds, the extraction process also releases some of the connective tissue repair factors that were embedded in the collagen matrix of the DBM. The released connective tissue repair factors are soluble in the DBM-derived extract solution.

The extraction may be conducted in medium that is an acid, alkaline or salt solution. Any of several acids may be used to perform the extraction. Such acids include hydrochloric acid, citric acid, acetic acid, lactic acid, and malic acid. Alternatively, any of several alkaline solutions (e.g., sodium hydroxide, or potassium hydroxide) or aqueous salts (such as lithium chloride) may be used to perform the extraction. Preferably, a carboxylic acid is used. Most preferably, citric acid is used.

The concentration of the acid, base, and/or salt may vary, depending on the effectiveness of the acid, base, or salt used as a hydrolytic agent. The amount of DBM placed in the acid, alkaline or salt solution may vary, depending on the strength of the solution and the shape and size of the DBM.

Preferably, where citric acid and granular or powdered DBM are used, about 10 to about 50 mL of about 1.0 to 10.0 M citric acid is used per gram of DBM. Most preferably, about 20 mL of about 2.0 to about 3.0 M citric acid is used per gram of DBM. The DBM and aqueous acid solution may be shaken, stirred, or otherwise agitated to speed this extraction process. Preferably the aqueous acid solution and DBM are stirred or agitated between about 2 and about 96 hours, and most preferably, between about 48 and about 72 hours. This extraction step may take place at any temperature below which endogenous proteins within the DBM begin to irreversibly denature. For the purpose of this invention, it is preferred that ambient temperature or room temperature is between about 15° C. and about 25° C., more preferably between about 18° C. and about 25° C., and further preferably between about 15° C. and 21° C.

By varying the parameters of the extraction system, the molecular weight and physical properties of the resulting gelatin can be affected. The pH and/or concentration of the system affect the protein composition of the extraction products. The ability of the system to extract proteins is based on both the pH and concentration of the DBM and extraction medium. For example, the extraction of collagen and conversion into gelatin via hydrolysis has been shown to be dependent on the pH of the extraction media (LaRoche, et al.; Lilja, et al.; Rainville, et al., supra). Similarly, the pH and/or concentration of the extraction media affect the protein composition of the extraction products. The relative concentrations of DBM and extraction medium during the extraction step also affect the ability and degree to which proteins are extracted.

The extraction step may also be performed under a vacuum. For example, demineralized bone particles and an extraction medium can be contacted in a flask attached to a vacuum line connected to a pump that supplies a vacuum, e.g., about 28 mm Hg vacuum.

Following DBM exposure to the extraction medium, the soluble extraction product is separated from the insoluble extraction product, which is generally in the form of an insoluble solid residue. This separation may occur by any of a number of processes, such as decanting, filtering, or centrifuging. Preferably, filtration is used. Optionally, water may be added to the remaining insoluble extraction product as a means of washing and collecting additional dissolved material. Preferably, this water wash step is performed, for example, by adding about 10 to about 100 mL of sterile deionized water per gram of DBM starting material, after which the mixture is stirred, shaken, or otherwise agitated then separated. Most preferably, about 20 mL of sterile deionized water is added per gram of DBM starting material, and the mixture is shaken then filtered. The liquid phase may be saved and later combined with the soluble extraction product to increase the product yield. Optionally, the extraction and separation steps may be repeated one or more times by adding fresh extraction medium to the residue followed by an aqueous wash. Following the repeat extractions and water washes, the extraction and water wash volumes may be saved and added to the extraction and/or water wash volumes from the first extraction to increase the product yield. The insoluble extraction product may be saved and used as described herein.

The soluble extraction product is next diluted, neutralized and/or the salts are removed. This also may occur by any of a number of processes, such as titration, dialysis, liquid-liquid extraction, or precipitation. Preferably, dialysis is used. A protein concentrator or ultrafiltration unit may be used before or during dialysis to speed the dilution, neutralization and/or salt removal processes. The neutralization and salt removal processes should eliminate a substantial portion of the soluble ions and small molecules in the soluble extraction product. Preferably, if an acid or basic extraction medium is used, the pH of the soluble extraction product is adjusted to between about 4 and about 10. Most preferably, if an acid extraction medium is used, the pH of the remaining soluble extraction product is adjusted to be between about 0.5 and about 5.5, further preferably between about 0.5 and about 3.5.

The neutralized, salt-free soluble extraction product is partially or fully dried to remove excess water. The drying may occur by various means. Preferably, the drying occurs by lyophilization (freeze drying). Preferably, the drying is complete, such that all water is removed and a dry product remains. Alternatively, the lyophilization or other drying process may be arrested at some time prior to completion, such that a variety of products exist in concentrated, but not completely dehydrated form. Such products are referred to as "concentrate" herein. The dried soluble extraction product generally has a white, fluffy appearance like cotton. The concentrate will have a greater moisture content and, therefore, may have the appearance of a gel, putty, or paste.

The dried soluble extraction product or concentrate may be partially or fully rehydrated to a fluid or plastic form, such as a gel, putty, or paste. The primary components of this material are water, DBM-derived proteins, and connective tissue proteins. The relative amounts of dry soluble extraction product and water in the mixture may be varied to adjust the viscosity and other physical characteristics of the mixture. Preferably, about 5 to about 15 mL of deionized water is added to about 0.1 to about 3.0 g of dry product, and most preferably about 10 mL of deionized water is added to about 0.8 g of dry product. The rehydration process may be aided by means of mechanical mixing, such as shaking or stirring at room temperature. Preferably, the rehydration is aided by stirring. Concentrate may be used in place of or in addition to dry product. Where concentrate is used, water or dry product may be mixed with concentrate to change the viscosity and other physical characteristics of the resulting mixture.

One or more biologically active ingredients may be added to the resulting composition. These active ingredients may or may not be related to the connective tissue repair capabilities of the composition. Suitable active ingredients include DBM and the insoluble extraction product containing residual, endogenous bone morphogenetic proteins and related proteins such as cartilage derived morphogenetic proteins (CDMPs). Other active ingredients that may be added to the composition, including bone-derived materials such as cortical or cancellous bone chips and bone mineral, osteogenic chemicals (e.g. L-arginine), osteogenic peptides (e.g. OSA), osteogenic growth factors (e.g. transforming growth factor-beta [TGF-β], insulin-like growth factor [IGF], platelet derived growth factor [PDGF], vascular endothelial growth factor [VEGF], fibroblast growth factor [FGF]), and recombinant BMPs (e.g rBMP-2, rBMP-7), fibronectin, and blood-derived proteins. When added in appropriate combinations, these active ingredients may assist bone repair, cartilage repair, ligament and tendon repair, meniscal repair, and other musculoskeletal applications.

One or more thickening materials may be added to the resulting composition. Any such material may also be an active ingredient or biologically inert. Suitable thickening materials include collagen, insoluble extraction product (which may or may not contain residual BMPs), bone mineral, hydroxyapatite, tricalcium phosphate, biphasic calcium phosphate, calcium sulfate, biological glasses, and natural or synthetic polymers. Such polymers include poloxamer 407 and related polymers. Where insoluble extraction product is used as a thickening material, it is preferably is washed with water to remove any residual extraction medium. Preferably, DBM, insoluble extraction product, and/or a reverse phase medium are used as a thickening material with or without added proteins. The reverse phase medium may be an aqueous mixture of PLURONIC F127 (BASF Corp.), a polyoxyalkylene ether of high molecular weight having water soluble, surface active, and wetting properties, in an amount sufficient to confer a reverse phase property to the composition, preferably an approximately 20-40% w/w, more preferably about 23-32% /w and further preferably about 25% w/w or about 35% w/w mixture of PLURONIC F127 and water. Other reverse phase media include aqueous mixtures of derivatives of PLURONIC F127, such as those disclosed in U.S. Provisional Patent Application Ser. No. 60/345,113, which is incorporated herein by reference.

The biological, physicochemical and biodegradation properties of the composition may be altered by known cross-linking agents such as chemicals (e.g., glutaraldehyde or formaldehyde) or radiation (e.g gamma or electron beam). Preferably radiation is used as the cross-linking agent, and most preferably electron beam (E-beam) radiation is used to irradiate the wet or dry materials at doses between about 5 and about 50 kGray.

The resulting composition may be used in several different manners. In one preferred embodiment, the composition is used as a coating for surgical implants. Preferably, the mixture is applied to lyophilized, cancellous bone chips; or cancellous bone chips are dipped into mixture. The bone chips, coated with the mixture, may be dried. The drying step may be conducted by any conventional drying process, including lyophilization or oven drying. Preferably, drying is by lyophilization. The coated bone chips may be used as or in surgical implants at, in, on, or near bone defect sites, cartilage repair sites, or other musculoskeletal sites. Alternatively, the coating may be applied to larger segments of bone, artificial implants, or any other kind of surgical implant.

In another preferred embodiment, the composition is injected or inserted at, in, on, or near a bone or chondral defect site. The manner of injection or insertion is not essential, but preferably injection is via syringe and insertion is by creating a surgical opening to access the bone or chondral defect site.

In another preferred embodiment, the composition is mixed with a combination of active and filler or thickening materials such as DBM and insoluble extraction product respectively, and injected or inserted at, in, on, or near a bone or chondral defect site. Preferably the weight to weight (w/w) ratio of DBM to insoluble extraction product is about 3 to 1.

Alternatively, the dry soluble extraction product or concentrate may be mixed with aqueous alcohol or other volatile solutions, cast into a desired shape and dried to form a sponge-like material. Preferably, a one to six carbon alcohol is used. Most preferably, ethanol is used. Preferably, a 1 to 20 percent alcohol by volume solution is used. Most preferably, a 4.75 percent ethanol by volume solution is used. Preferably, 20 mg to 200 mg of dry material are combined with each mL of ethanol. Preferably, 50 to 80 mg of dry soluble extraction product per mL of ethanol are used. A biologically active ingredient, as discussed above, may also be added. Preferably, DBM is used. Additionally, one or more thickening materials, as discussed above, may also be added. Insoluble extraction product may also be added to this composition.

The resulting composition may be cast into a sheet or other shape with or without other added materials. The sheet or other shape is dried. Drying may be done by any conventional method, including lyophilization or air-drying. Preferably, drying is by lyophilization.

In a preferred embodiment, the sheet or shape formed with an alcohol solution as described above is used as or as part of a surgical implant. Preferably, where a sheet is used, it is used as a wrap around an area or as a patch inserted into a bone defect site, e.g., insertion into a bone defect, a chondral defect, a spinal fusion cage or a pre-reamed acetabular bed.

In a further preferred embodiment, the dried soluble extraction product, which is in the form of a white, fluffy material is used to make a sponge-like material that contains demineralized bone particles. The white, fluffy material may be chopped into small pieces of about 0.5 to about 5 cm, more preferably about 1 to about 2 cm. The chopped material is then combined with aqueous ethanol (approximately 3-10% ethanol, more preferably about 4-5% ethyl alcohol), and mixed until the white, fluffy material is dispersed. DBM particles are then added at a ratio of about 2-4:1 by weight, more preferably 3:1 by weight and the composition is thoroughly mixed. Then, ethanol is added to the composition and the mixed composition is poured into a container, preferably a container that is in the shape of the desired product. The composition is then refrigerated, frozen and lyophilized to obtain a composition that is substantially free of moisture. The end product has a sponge-like consistency.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

2.0 M-2 Day Extraction With Citric Acid

Twenty mL of 2.0 M citric acid is added per gram of DBM in a 500 mL polypropylene centrifuge tube. The citric acid and DBM are stirred at room temperature for 48 hours. The DBM/solvent dispersion is filtered through a 100 μm mesh. The residual that does not pass through the mesh is further washed with water. The wash is filtered and combined with the original filtrate. The filtrate and residual are saved and set aside.

Example 2

3.0 M-2 Day Extraction With Citric Acid

Twenty mL of 3.0 M citric acid is added per gram of DBM in a 500 mL polypropylene centrifuge tube. The citric acid and DBM are stirred at room temperature for 48 hours. The DBM/solvent dispersion is filtered through a 100 μm mesh. The residual that does not pass through the mesh is further washed with water. The wash is filtered and combined with the original filtrate. The filtrate and residual are saved and set aside.

Example 3

3.0 M-3 Day Extraction With Citric Acid

Twenty mL of 3.0 M citric acid is added per gram of DBM in a 500 mL polypropylene centrifuge tube. The citric acid and DBM are stirred at room temperature for 72 hours. The DBM/solvent dispersion is filtered through a 100 μm mesh. The residual that does not pass through the mesh is further washed with water. The wash is filtered and combined with the original filtrate. The filtrate and residual are saved and set aside.

Example 4

3.0 M-5 Day Sequential Extraction With Citric Acid

Twenty mL of 3.0 M citric acid is added per gram of DBM in a 500 mL polypropylene centrifuge tube. The citric acid and DBM are stirred at room temperature for 24 hours. The DBM/solvent dispersion is filtered through a 100 μm mesh. The filtrate is separated and saved for further processing. The residual that does not pass through the mesh is recombined with fresh citric acid (20 ml/g of starting DBM) and stirred for an additional 24 hours. This process is repeated for five days, such that five extractions will have occurred. The filtrate from each isolation step is kept separate for individual processing. At the fifth day, the residual is rinsed with de-ionized water (20 ml/g of starting DBM) which is combined with the original filtrate. The filtrate and residuals are saved and set aside.

Example 5

Neutralization and Lyophilization of Supernatant

The filtrate from Example 1, 2, 3, or 4 is placed in dialysis tubing (pore size 8,000-10,000 KDa) and dialyzed against deionized water until the pH of the supernatant portions reaches a minimum of 5. At this point, the filtrate is transferred to a lyophilization flask, shell frozen, then placed on a lyophilizer. This lyophilate is referred to below as the soluble portion.

Example 6

Processing the Residue

The resulting insoluble particles from Example 1, 2, 3, or 4 are washed with 200 mL $H_2O$ per gram DBM. This wash is repeated until the particles reach a pH of 4-8; the wash liquids are discarded. The insoluble particles are lyophilized to obtain a dry insoluble material.

Example 7

Formulation of an Extrudable Gel

The soluble portion from Example 5 is dissolved in deionized water at a concentration of 0.08 g soluble portion per ml water. The mixture is stirred at room temperature for approximately 15 minutes to 1 hour or until the mixture becomes homogenous. At this point the soluble portion will have dissolved and a gel begins to form. Gelling may be accelerated by cooling the suspension/solution to about 1 to 10° C. The gel is placed at 4° C. for 15 minutes to accelerate gel formation or is left at room temperature for 1 hour. The resulting gel is stable at room temperature. This gel may be osteoinductive at certain concentrations and used for percutaneous injection or surgical implantation at, in, on, or near bone fracture or defect sites. This gel may be mixed with additional active or inactive materials.

Example 8

Formulation of an Extrudable Product With Poloxamer 407 as a Thickening Material Soluble portion from Example 5 is dissolved in deionized water at a concentration of 0.04 g/ml. The resulting gel (10 ml) is mixed with 20 mL of a 35% w/w poloxamer 407 gel. The mixture is stirred at room temperature for several minutes or until the mixture becomes homogenous and opaque. This gel may be osteoinductive at certain concentrations and may be used for percutaneous injection or surgical implantation at bone defect sites or mixed with additional active or inactive fillers to create a putty or paste-like consistency.

Example 9

Formulation of an Extrudable Product With Insoluble Portion as a Thickening Material An extrudable gel, putty or paste is produced by mixing 2.0 ml of the gel from Example 7 with 0.4 g of the insoluble particles from Example 6. The mixture is stirred at room temperature for several minutes until a gel, putty, or paste consistency has been obtained. This material may be used for injection or surgical implantation at, in, on, or near bone and/or chondral defect sites.

Example 10

Formulation of an Extrudable Product With DBM as an Active Material

An extrudable gel, putty or paste is produced by mixing 2.0 ml of the gel from Example 7 with 0.6 g of DBM. The mixture is stirred at room temperature for several minutes until a gel or putty consistency has been obtained. This material may be used for injection or surgical implantation at, in, on, or near bone and/or chondral defect sites.

Example 11

Formulation of an Extrudable Product With DBM and Insoluble Particles as Thickening Material An extrudable gel, putty or paste is produced by mixing 4.76 ml of the gel from example 7 with 1.02 g of DBM and 0.24 g of the insoluble particles from Example 6. A similar putty with 1.02 g of insoluble residual and 0.24 g of DBM may also be obtained. The mixture is stirred at room temperature for several minutes until a gel or putty consistency has been obtained. This gel may be used for injection at, in, on, or near bone and/or chondral defect sites.

Example 12

Formulation of an Extrudable Putty With Both Poloxamer 407 and Insoluble Portion as Thickening Materials The gel from Example 8 (3.0 ml) is mixed with 1.5 g of the insoluble particles from Example 6. The mixture is stirred at room temperature for several minutes until a putty consistency has been obtained. This material may be used for injection or surgical placement at, in, on, or near bone and/or chondral defect sites.

Example 13

Formulation of an Extrudable Putty With Poloxamer 407, DBM, and Insoluble Portion as Thickening Materials The gel from Example 8 (3.0 ml) is mixed with 1.2 g of DBM and 0.3 g of the insoluble particles from Example 6. A similar putty can be formed from 1.2 g of the insoluble particles from Example 6 and 0.3 g of DBM. The mixture is stirred at room temperature for several minutes until a putty consistency has been obtained. This material may be used for placement at, in, on, or near bone and/or chondral defect sites.

Example 14

Formation of Shapes or Sheets From Insoluble and Soluble Products

The dry soluble portion from Example 5 is dissolved in a 4.75% v/v ethanol solution in water. Specifically, 1.2 g of the soluble portion was dissolved in 40 mL of 4.75% v/v ethanol. Once a homogeneous solution is obtained, 2.3 g of insoluble particles from example 6 are added. The dispersion is thoroughly mixed and cast as a sheet. The mix is immediately frozen and then lyophilized. Cancellous bone and/or DBM may also be added alone as insoluble particles or in combination with one another. This material may be used for placement at, in, on, or near bone and/or chondral defects.

Example 15

Use of an Extrudable Product as Osteogenic Coating

The DBM derived product from Examples 1-14 is used to coat a surgical bone implant. The coated implant is lyophilized. The lyophilized product may be inserted at, in, on, or near a bone and/or chondral defect site.

Example 16

Formulation of an Extrudable Product Containing Cancellous Bone With or Without the Addition of Blood or Bone Marrow The DBM-derived gel and putty products from Examples 1-15 are combined with cancellous bone material to produce a gel or putty with different handling characteristics. In addition, the cancellous containing gel/putty can be combined with blood and/or bone marrow to provide a growth factor-enriched osteogenic material.

Example 17

Illustrations of Bone Inductive Properties

Samples from Example 1 (25 mg lyophilized soluble material alone), Example 2 (25 mg lyophilized soluble material alone), Example 3 (25 mg rehydrated residual), Example 8 (25 mg of product as described in Example 8 plus DBM and residual), and Example 10 (25 mg of product as described in Example 10) were prepared for implantation. These samples, along with samples of active DBM used to create the samples, were sterilized using electron-beam technology and implanted into the musculature of athymic (rhu/rhu) mice, according to IACUC approved protocols. The mice were anesthetized using a ketamine/xylazine mixture for induction and maintenance of anesthesia throughout the procedure. General anesthesia was accomplished in approximately 3-5 minutes and was verified by a lack of response to a toe pinch.

The dorsal area of each mouse was swabbed using betadine/alcohol scrub. Each mouse was placed in dorsal recumbency. Then using a scalpel or scissors, a 1 cm incision was made in the skin. A 1.0 mm incision was made in the muscle and blunt dissection was used to expand the implantation site. All implants were placed between the muscle bundles. The procedure was repeated on the contralateral side through the same skin incision. Wound closure was accomplished with one or two vicryl sutures for muscle closure and using stainless steel wound clips for the skin incision. Post-operative checks were made to ensure animals fully recover from the procedure.

On day 28 post-operatively, all animals were anesthetized with sodium pentobarbital and sacrificed by cervical dislocation. After euthanasia, the skin over the implant was reflected and both implants were removed. The right implant from each animal was placed in 10% neutral buffered formalin for histology and the left implant from each animal was placed in cryovials then flash frozen in liquid nitrogen for alkaline phosphatase analysis. Frozen specimens were stored at −80° C. for subsequent biochemical analysis. The remaining specimens were placed in 10% v/v neutral buffered formalin prior to histological processing. These samples were processed and embedded in paraffin. Decalcified paraffin embedded histological sections were prepared and stained with haematoxylin and eosin. Qualitative analysis was performed to evaluate each sample for bone inductivity. Samples from each paraffin embedded section were also evaluated quantitatively to determine the amount of newly formed bone as a function of total implant area.

Figure 1B:
FIG. 1B is a photograph that shows the same sample at a different site. Additional new bone (arrows) and bone marrow (B) is apparent. Residual material (R) is also present in this site. Haematoxylin and eosin stain; original magnification ×200.
Figure 2A:
FIG. 2A is a photograph of the composition of Example 2 plus DBM putty implanted for 28 days in an athymic mouse. The photograph shows multiple foci of new bone (arrows) and bone ossicles surrounding fatty bone marrow. Residual DBM is still present in this explant. Haematoxylin and eosin stain; original magnification ×100.
Figure 2B:
FIG. 2B is a photograph at higher magnification, wherein the woven nature of the new bone of one of the ossicles seen in FIG. 2A is apparent. The woven bone surrounds an area of healthy bone marrow (BM). Haematoxylin and eosin stain; original magnification ×400.

The results from this study show that 25 mg (containing a little over 3 times the amount of soluble portion present in the putty formulations) of 2.0 M-2 day lyophilized soluble material (soluble portion) alone is non-inductive in this model. Conversely, 25 mg (a little over 3 times the amount of soluble portion present in the putty formulations) of 3.0M-2 day lyophilized dry material (soluble portion) is inductive such that very small ossicles formed in 5 of the 6 samples evaluated. The 2.0 M-2 day plus DBM putty (FIGS. 1A and 1B) and the 3.0 M-2 day plus residual DBM putty (FIGS. 2A and 2B) were also inductive in this model.

Example 18

Preparation of Bone Repair Composition

This process is conducted primarily at room temperature in a manufacturing environment with a controlled temperature of about 59-70° F. (15-21° C.). Certain steps are conducted well below room temperature, including freezing and lyopholization (freeze-drying) steps.

Demineralized bone matrix (DBM) particles are obtained from an AATB accredited or other tissue bank or prepared by demineralizing mineralized bone by conventional methods. One lot of DBM particles is divided into a first portion (approximately 60% of the lot) and a second portion (approximately 40% of the lot). The DBM particles are then placed in an Erlenmeyer flask outfitted with a perforated Teflon™ baffle. A 3 M citric acid solution is added (20 ml of acid per gram of DBM particles). The flask stopper is outfitted with a fixture for attachment of a vacuum line connected to a pump supplying about 28 mm Hg vacuum. The assembly is affixed to an orbital shaker providing vigorous agitation. Vacuum and agitation are applied for 72 hours. Alternatively, this process can be conducted without application of a vacuum. During this time, the temperature of the flask contents are at or slightly below room temperature. After 72 hours, the flask contents consist of two portions: an acidic liquid containing the soluble part of the DBM particles and an insoluble solid particulate.

The entire contents of the flask is vacuum filtered through a 350 micron screen on a Buchner funnel to separate the insoluble solid particulate from the acidic liquid containing the soluble part of the DBM particles. Both parts are retained.

The insoluble solid particulate is rinsed multiple times with room temperature deionized water in an ultrasonic cleaner. The washed particles are drained, placed in sealed Tyvek™ bags, or other suitable container, deep frozen in a freezer maintained at about −75 to −80° C., and then lyophilized for 5-7 days. After lyophilization, the cooling source is automatically turned off and the particles return to room temperature.

The acidic liquid portion obtained from the filtering step is dialyzed for 72 hours in room temperature deionized water. The dialyzed material is then placed in sealed containers, deep frozen in a freezer maintained at −75 to −80° C., then lyophilized over several days to remove water.

Two separate and distinct components result from these processing steps: a light, dry, essentially white, fluffy material from the solubilized portion of the DBM particles and a yellowish, dry particulate from the insoluble solid particles.

Then, the two components are combined at room temperature. First, the fluffy component (dried soluble extraction product) is placed in a disinfected plastic container and partially dissolved in room temperature distilled water. The pH is then adjusted to about 1.8-2.2 over several minutes by dropwise addition of room temperature 3 M citric acid. Then, the insoluble solid particles and the second portion of the DBM particles are added and mixed.

This final formulation is introduced into syringes and chilled at refrigerator temperature (about −4° C.) for 8-72 hours.

The raw materials, intermediate materials or final product may be sterilized, for example, by electron beam ("E-beam") sterilization treatment, preferable at a target dose within 5-25 kilograys (kGy).

Example 19

Preparation of Bone Repair Composition in the Form of a Sponge

This process is conducted primarily at room temperature in a manufacturing environment with a controlled temperature of about 59-70° F. (15-21° C.). Certain steps are conducted well below room temperature, including freezing and lyopholization (freeze-drying) steps.

The dried soluble extraction product as prepared in Example 18 is used for this process. 2.5137 grams of DBM particles and 826.87 milligrams of the white, fluffy dried soluble extraction product are weighed. The white, fluffy material is chopped into small pieces of about 1 to about 2 cm. The chopped material is placed into a centrifuge tube (approximately 50 ml tube) or other similarly sized container. About 35 ml of refrigerated 4.75% ethanol is added to the centrifuge tube and the contents are aggressively mixed, for example, with a vortex mixer for approximately 3 minutes or until the white, fluffy material is dispersed. The DBM particles are then added to the centrifuge tube and the contents are aggressively mix for another 1 minute or until the contents are thoroughly and uniformly mixed. Ethanol is then added to the tube such that the contents fill the tube, for example, about 40 ml. The contents of the tube is again aggressively mixed for about 15 seconds or until thoroughly mixed.

The mixture is then poured into a tray having the shape of the desired product. The tray is placed in a refrigerator (~4° C.) for about an hour or until a firm gel is obtained. The tray is then transferred to a freezer of about −84° C. for at least 3 hours. The composition is then lyophilized for about 24 hours, or until the composition is substantially free of moisture. The end product has a sponge-like consistency. The thickness may vary, but preferably is 1/8" to about 1" thick, more preferably about 1/4" thick.

What is claimed is:

1. An osteogenic composition comprising: demineralized bone particles enriched with dried, acid-soluble, demineralized bone extraction product derived from demineralized bone contacted with an acidic extraction medium at a pH of between 0.5 and 5.5 and at an extraction temperature between about 15° C. and 25° C.; and
   a thickening material selected from the group consisting of collagen, insoluble extraction product, calcium phosphate, hydroxyapatite, tricalcium phosphate, biphasic calcium phosphate, calcium sulfate, biological glass, natural polymer, synthetic polymer, poloxamer, and reverse phase medium.

2. The osteogenic composition of claim 1, further comprising a bone morphogenetic protein.

3. The osteogenic composition of claim 1, further comprising an active ingredient selected from the group consisting of bone morphogenetic protein, cartilage derived morphogenetic protein, cortical bone, cancellous bone, bone mineral, osteogenic chemical, osteogenic peptide, osteogenic growth factor, recombinant bone morphogenetic protein, fibronectin, blood, bone marrow and blood-derived protein.

4. The composition of claim 1, wherein said dried, acid-soluble, demineralized bone extraction product is a white, fluffy substance.

5. The composition of claim 1, wherein said dried, acid-soluble, demineralized bone extraction product is further combined with ethanol or water, and an active ingredient selected from the group consisting of bone morphogenetic protein, cartilage derived morphogenetic protein, cortical bone, cancellous bone, bone mineral, osteogenic chemical, osteogenic peptide, osteogenic growth factor, recombinant bone morphogenetic protein, fibronectin, blood, bone marrow and blood-derived protein.

6. The composition of claim 5, wherein the product is further dried after combining with said ethanol or water and said active ingredient.

7. The composition of claim 6, wherein said product is dried by lyophilization.

8. The composition of claim 1, wherein the form of said composition is selected from the group consisting of gel, paste, putty and sponge.

9. An osteogenic composition comprising a dried, acid-soluble extraction product derived from demineralized bone contacted with extraction medium at a pH of between 0.5 and 5.5 and at an extraction temperature between about 15° C. and 25° C. and further including a reverse phase medium.

10. An osteogenic composition comprising a dried, acid-soluble extraction product derived from demineralized bone contacted with extraction medium at a pH of between 0.5 and 5.5 and at an extraction temperature between about 15° C. and 25° C.

11. An osteogenic composition comprising a dried, acid-soluble extraction product derived from demineralized bone contacted with extraction medium at a pH of between 0.5 and 5.5 and at an extraction temperature between about 15° C. and 25° C. and further including demineralized bone particles.

12. The osteogenic composition of claim 9 further including demineralized bone.

13. The osteogenic composition of claim 9 further including cancellous bone.

14. The osteogenic composition of claim 9 further including bone marrow.

15. The osteogenic composition of claim 10 further including cancellous bone.

16. The osteogenic composition of claim 10 further including bone marrow.

17. An osteogenic composition comprising: demineralized bone particles enriched with dried, acid-soluble, demineralized bone extraction product derived from demineralized bone contacted with extraction medium at a pH of between 0.5 and 5.5 and at an extraction temperature between about 15° C. and 25° C.; and collagen.

18. An osteogenic composition comprising: demineralized bone particles enriched with dried, acid-soluble, demineralized bone extraction product derived from demineralized bone contacted with extraction medium at a pH of between 0.5 and 5.5 and at an extraction temperature between about 15° C. and 25° C.; collagen and tricalcium phosphate.

19. An osteogenic composition comprising: demineralized bone particles enriched with dried, acid-soluble, demineralized bone extraction product derived from demineralized bone contacted with extraction medium at a pH of between 0.5 and 5.5 and at an extraction temperature between about 15° C. and 25° C.; collagen, tricalcium phosphate and reverse phase medium.

* * * * *